United States Patent [19]

Kawasaki et al.

[11] Patent Number: 5,398,551
[45] Date of Patent: Mar. 21, 1995

[54] ULTRASONIC TESTING METHOD FOR BALLS

[75] Inventors: Keiji Kawasaki, Nagoya; Koji Fushimi, Gifu, both of Japan

[73] Assignee: NGK Insulators, Ltd., Nagoya, Japan

[21] Appl. No.: 257,571

[22] Filed: Jun. 9, 1994

Related U.S. Application Data

[63] Continuation of Ser. No. 571,349, Aug. 23, 1990, abandoned.

[30] Foreign Application Priority Data

Aug. 30, 1989 [JP] Japan ................... 1-223939

[51] Int. Cl.⁶ ............................................ G01M 13/04
[52] U.S. Cl. ............................................ 73/593; 73/629
[58] Field of Search ............... 73/579, 593, 620, 621, 73/627, 629, 584

[56] References Cited

U.S. PATENT DOCUMENTS

| | | | |
|---|---|---|---|
| 4,281,548 | 8/1981 | Köber | 73/593 |
| 4,287,770 | 9/1981 | Weyns | 73/632 |
| 4,387,596 | 6/1983 | Fenkner et al. | 73/593 |
| 4,969,361 | 11/1990 | Kawasaki et al. | 73/593 |
| 5,005,417 | 4/1991 | Kawasaki et al. | 73/593 |

FOREIGN PATENT DOCUMENTS

| | | | |
|---|---|---|---|
| 0373603 | 6/1990 | European Pat. Off. | |
| 2855143 | 12/1978 | Germany | |
| 3810906 | 11/1988 | Germany | |
| 0054156 | 3/1987 | Japan | 73/627 |

OTHER PUBLICATIONS

The Way Things Work, pp. 138–139 ©1967.

Primary Examiner—Kenneth A. Wieder
Assistant Examiner—Raymond Y. Mah

[57] ABSTRACT

An ultrasonic testing method for detection of flaws in a ball-shaped material to be tested using an ultrasonic probe, wherein a test frequency f (MHz) of the probe and a radius of curvature r (mm) of a tip portion of the probe satisfy the relationship $50 \text{ mm} \leq r\sqrt{f} \leq 60 \text{ mm}$, and wherein the radius of curvature r (mm) of the tip portion and the diameter D (mm) of an oscillator of the probe satisfy the relationship $0.35 \text{ mm} \leq D/r \leq 0.50 \text{ mm}$. The method enables detection of surface and internal flaws in materials, particularly ceramic ball hearings having a diameter ranging from several tens of millimeters down to 10 mm or below.

6 Claims, 2 Drawing Sheets

ULTRASONIC TESTING METHOD FOR BALLS

This application is a continuation of application Ser. No. 07/571,349, filed Aug. 23, 1990 (now abandoned).

BACKGROUND OF THE INVENTION AND RELATED ART STATEMENT

This invention relates to an ultrasonic testing method for detection of flaws in balls, and more particularly to an ultrasonic testing method for balls in which the accuracy of flaw detection is enhanced by specifying the test frequency of a probe, the radius of curvature of a tip portion of the probe and the diameter of an oscillator of the probe.

As a testing method for detection of flaws in steel materials, steel plates, forgings, etc., there has hitherto been used an immersion type ultrasonic testing method.

The conventional immersion type ultrasonic testing is generally used where the material to be tested is comparatively large and the flaws to be detected are as large as several millimeters or above. Therefore, the testing system used for the conventional ultrasonic testing is not a special one. Also, the probe used for transmission and reception of an ultrasonic wave during testing is an ordinary one, namely, an immersion type probe which has a simple planar oscillator with a large diameter.

For products to be used under such severe conditions that even minute flaws, if any, would cause problems in practical use of the products, a system for ultrasonic detection of even minute flaws ranging down to several hundreds of micrometers in size has been adopted, in order to enhance reliability of flaw detection.

In an ultrasonic testing method for detecting minute flaws, a focus-type probe in which a concave resin lens is attached to the above-mentioned planar oscillator or in which the oscillator itself is shaped to be concave has been used.

In addition, research has been made in recent years on the use of ceramics for bearing members and the like, which are particularly required to have high reliability.

Because such ceramics are brittle materials, a testing method with high resolution has been desired for detection of flaws in ceramic products. In the recent art of ultrasonic testing for detection of flaws in ceramics and the like, therefore, attempts have been made to enhance the sensitivity and accuracy of flaw detection by raising the test frequency from previously used values of about 0.5–10 MHz to higher values of 15–100 MHz or by using a computer to perform image processing, and so on.

In application of the above-mentioned prior art, however, the materials to be tested have been limited to comparatively large products of a simple shape, such as flat plates, circular cylinders, prisms, circular tubes, etc. Also, the flaws detected have been limited to flaws being not smaller than 0.5 mm, at best, and located at a depth of several millimeters or more from the surface of the material under test. Accordingly, attempts to detect flaws in the surface and sub-surface of products having radii of curvature of 10 mm or less, such as a ball bearing, by the prior art have failed because of scattering and reflection of the transmitted ultrasonic wave at the surface of the product and because of complicated refraction of the propagated ultrasonic wave.

An ultrasonic testing method for detection of minute flaws in the surface, and within a depth of 2 mm from the surface, of bearing rolling elements in the form of balls, cylinders or the like has been proposed in Japanese Patent Application Laid-Open (KOKAI) No. 63-243751 (1988) corresponding to USSN 172244. In this method, a focus-type probe and the rolling element as the material to be tested are disposed with a predetermined amount of eccentricity therebetween, and ultrasonic flaw detection is carried out to detect minute flaws in the surface and the sub-surface of the material. The method, however, is not applicable to materials to be tested which have a radius of curvature of not more than 10 mm or which have a special curved surface.

SUMMARY OF THE INVENTION

It is an object of this invention to provide a testing method for detection of minute flaws, particularly in ceramic balls for bearings and other ceramic parts for engines, gas turbines, etc., which have recently been developed and which have small radii of curvature.

It is a particular object of this invention to provide an ultrasonic testing method which enables detection of minute flaws in the surface and the inside of ball-shaped parts having a comparatively small radius of curvature, ranging from several tens of millimeters down to 10 mm or below.

According to this invention, there is provided an ultrasonic testing method for detection of flaws in balls by use of an ultrasonic probe, wherein a test frequency f (MHz) of the probe and the radius of curvature r (mm) of a tip portion of the probe satisfy the relationship of the formula (1) given below, and the radius of curvature r (mm) of the tip portion of the probe and the diameter D (mm) of an oscillator of the probe satisfy the relationship of the formula (2) given below.

$$50 \leq r\sqrt{f} \leq 60 \quad (1)$$

$$0.35 \leq D/r \leq 0.50 \quad (2)$$

In the method according to this invention, a probe conforming to the curved surface of the material to be tested can be used. For instance, when the material to be tested has a spherical surface, a probe in which a tip portion thereof, namely, an acoustic lens or an oscillator, opposed to the material to be tested has a spherical surface is used. When the material to be tested has a cylindrical surface, a probe in which a tip portion thereof, namely, an acoustic lens or an oscillator, has a cylindrical surface is used. By use of such a probe in the ultrasonic testing method according to this invention, it is possible to make an ultrasonic wave incidence on the searching surface without scattering, and to more accurately detect flaws in the material to be tested which has a curved surface with a radius of curvature of not more than several tens of millimeters.

DETAILED DESCRIPTION OF THE PREFERRED EMBODIMENTS

The probe used in this invention will be described below while referring to FIG. 1.

Figure 1:
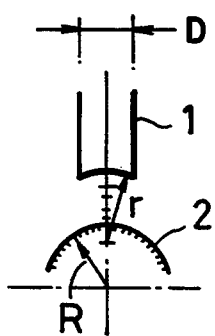
FIG. 1 is a sectional view illustrating the relationship between a probe used in this invention and the material to be tested which has a curved surface portion.

FIG. 1 is a conceptual view, in section, for illustrating the relationship between the probe used in this invention and the material to be tested which has a curved surface portion. The expression "the tip portion of the probe" used herein means an oscillator or an acoustic lens, as has been mentioned.

Referring to FIG. 1, the tip portion of the probe 1 which is opposed to a ball 2, or the material to be tested, is shaped to have a curved surface complementary to the curved surface of the material to be tested, for instance, a spherical surface. Where testing is conducted by setting the center axis of the probe to coincide with a center axis of curvature of the curved surface of the ball 2, the radius of curvature r of the curved surface of the tip portion is set to be from 0.5 to 2.0 times the radius of curvature R of the ball 2. Where testing is conducted by setting an eccentricity between the center axis of the probe and the center axis of curvature of the ball 2, the radius of curvature r of the tip portion is set to be from 1.0 to 3.0 times, preferably from 1.5 to 2.5 times, the radius of curvature R of the ball 2.

Furthermore, in the ultrasonic testing method of this invention, when testing is conducted by setting an eccentricity between a center axis of curvature of the curved surface portion of the material to be tested and the center axis of the probe, an adjustment is made so that the angle of refraction of the ultrasonic wave will be 90°.

Figure 4:
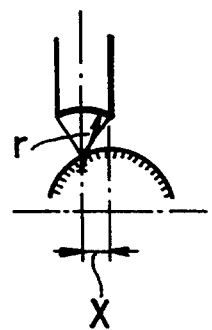
FIG. 4 is a sectional view illustrating the relationship between the focus of the probe and the material to be tested which has a curved surface portion, according to one embodiment of this invention.

The eccentricity quantity which ensures that the angle of refraction of the ultrasonic wave is 90° can be calculated from, for example, the following formula (3):

$$X = R \cdot V_L / V_B \quad (3)$$

where, as shown in FIG. 4, X is the eccentricity quantity of the probe 1, $V_L$ (m/sec) is the velocity of ultrasonic longitudinal wave in the liquid (e.g., water) in which the ultrasonic testing device is placed, and $V_B$ (m/sec) is the velocity of an ultrasonic transverse wave in the material to be tested (e.g., ball) 2.

Figure 2:
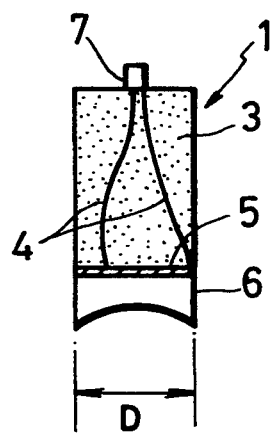
FIGS. 2 and 3 are each an illustrative sectional view of a probe according to one embodiment of this invention.
Figure 3:
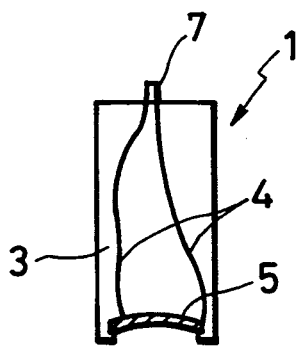

Moreover, as shown in FIG. 2 or FIG. 3, the probe 1 used in this invention has an oscillator 5 connected to lead wires 4 extended from a connector 7 for connection to an ultrasonic transmitter-receiver through a damper 3. Thus, the tip portion of the probe which is opposed to the material to be tested is an acoustic lens 6 making intimate contact with the oscillator 5, or is the oscillator 5 itself. In this invention, the acoustic lens 6 or the oscillator 5 can be used for the probe, after being provided with a curved surface the kind of which and the radius of curvature of which are set in accordance with those of the curved surface of the ball 2 (namely, the material to be tested).

Further, in the ultrasonic testing method of this invention, testing is conducted by use of a probe in which the test frequency f (MHz) and the radius of curvature r (mm) of the tip portion of the probe are so set that the relationship of the following formula (1):

$$50 \leq r\sqrt{f} \leq 60 \quad (1)$$

is established and that the radius of curvature r (mm) of the tip portion of the probe and the oscillator diameter D (mm) satisfy the relationship of the formula (2) $0.35 \leq D/r \leq 0.50$. By use of such a probe, it is possible to detect, with good accuracy, minute flaws in the surface and the inside of a material to be tested, particularly a ball-shaped material, which has a curved portion with a radius of curvature of several tens of millimeters or below.

The relationship of the formula (1) and the relationship of the formula (2) between the radius of curvature of the tip portion of the probe and the diameter of the oscillator as mentioned above have been found out as a result of the present inventors' experiments and investigations on the probe, test frequency and the like. That is to say, accurate detection of minute flaws is achievable by ultrasonic testing with a probe which, in FIG. 6, falls in the region between the curve $r = 60/\sqrt{f}$ and the curve $r = 50/\sqrt{f}$ and which has a D/r value in the range of $0.35 \leq D/r \leq 0.50$.

The method according to this invention is an ultrasonic testing method constituted as described above, by which it is possible to detect, with good accuracy, minute flaws in the surface and the inside of a structural member or part, such as a ceramic ball, having a curved surface portion, particularly, with a radius ranging from several tens of millimeters down to 10 mm or below.

EXAMPLE

A preferred embodiment of this invention will now be described in detail below while referring to the drawings; it is to be understood, however, that the invention is not limited to the following embodiment.

Example 1

Figure 5:
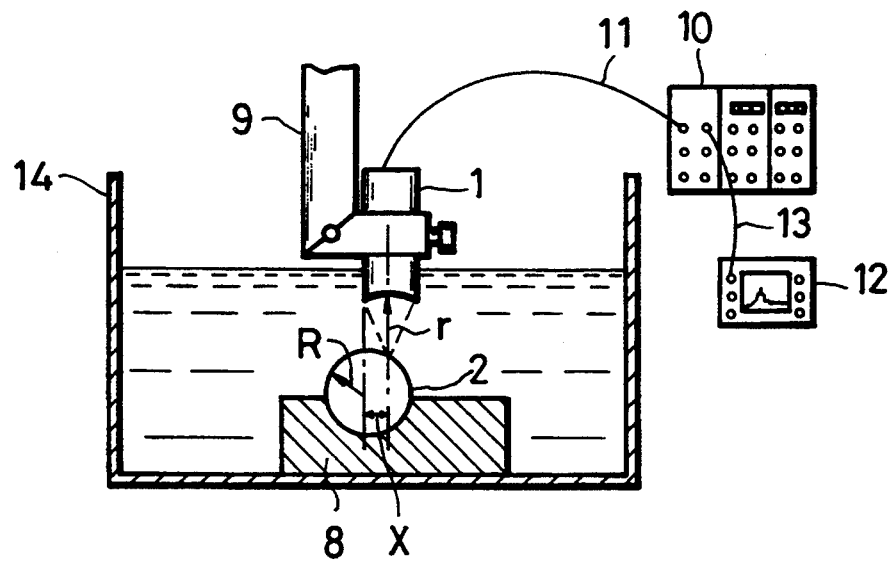
FIG. 5 is a sectional view illustrating one embodiment of an ultrasonic testing method of this invention.

FIG. 5 is a sectional view illustrating one embodiment of an ultrasonic testing method according to this invention.

Four kinds of silicon nitride balls 10 mm in diameter were prepared which were provided therein with pores respectively 50, 100, 300 and 500 μm in diameter, by mixing resin particles into the raw material for the balls. Referring to FIG. 5, the silicon nitride ball 2 was first set on a ball holder 8 disposed in a water tank 14 and designed to enable free manual rotation of the ball, namely, the material to be tested. A probe 1 which had a test frequency of 50 MHz and in which an oscillator surface of a tip portion of the probe was a concave spherical surface with a radius of curvature of 7.5 mm and an oscillator diameter of 3 mm was set on a probe holder 9. An eccentricity X of 1.3 mm was set between the ball 2 and the center axis of the probe so that the angle of refraction of an ultrasonic wave would be 90°. Further, the probe holder 9 was adjusted so that the spacing between the oscillator of the probe and the surface of the ball was 7.5 mm, the value being equal to the radius of curvature of the probe. The probe 1 was connected through a high-frequency cable 11 to an ultrasonic transmitter-receiver 10 disposed in the exterior of the water tank. For observation of an ultrasonic echo reflected from the ball, an oscilloscope 12 was connected to the ultrasonic transmitter-receiver 10 by a high-frequency cable 13. In this condition, the echo was observed on the oscilloscope 12 while the silicon nitride ball 2 was manually rotated. After observation of the echo for the entire surface of the silicon nitride ball 2, the ball 2 was replaced by another one, and this procedure was repeated until all the silicon nitride balls were tested. As a result, all the flaws having a diameter of 50 μm at a minimum were capable of being detected (Experiment No. 1).

Next, the probe was replaced by a probe which had a test frequency of 50 MHz and in which the oscillator surface was a concave spherical surface with a radius of curvature of 10 mm and an oscillator diameter of 5 mm, and the same experiment as above was carried out. It was possible to detect flaws ranging down to 100 μm in diameter (Experiment No. 2).

The experiment as above was then repeated by use of a probe which had a test frequency of 50 MHz and in which the oscillator surface was a concave spherical surface with a radius of curvature of 15 mm and an oscillator diameter of 6.4 mm (Experiment No. 3), probes which had a test frequency of 15 MHz and in which the oscillator surface was a spherical surface with an oscillator diameter of 6.4 mm and a radius of curvature of 15 mm (Experiment No. 4), 12 mm (Experiment No. 5) or 10 mm (Experiment No. 6), probes which had a test frequency of 25 MHz and in which the oscillator surface was a concave spherical surface with a radius of curvature of 15 mm and an oscillator diameter of 6.4 mm (Experiment No. 7) or with a radius of curvature of 10 mm and an oscillator diameter of 5 mm (Experiment No. 8), and probes which had a test frequency of 35 MHz and in which the oscillator surface was a concave spherical surface with a radius of curvature of 7.5 mm and an oscillator diameter of 3 mm (Experiment No. 9) or with a radius of curvature of 10 mm and an oscillator diameter of 5 mm (Experiment No. 10).

In Experiment Nos. 4 and 8, it was possible to detect all flaws. The experiment was further repeated by use of the same probe as used in Experiment No. 4 except that the oscillator diameter was 10 mm (Experiment No. 11), and also by use of the same probe as used in Experiment No. 8 except that the oscillator diameter was 3 mm (Experiment No. 12). In the last two experiments (Experiment Nos. 11 and 12), it was impossible to detect all flaws, due to the change in D/r as compared with the former corresponding experiments (Experiment Nos. 4 and 8).

The results of the above experiments are shown in Table 1.

Figure 6:
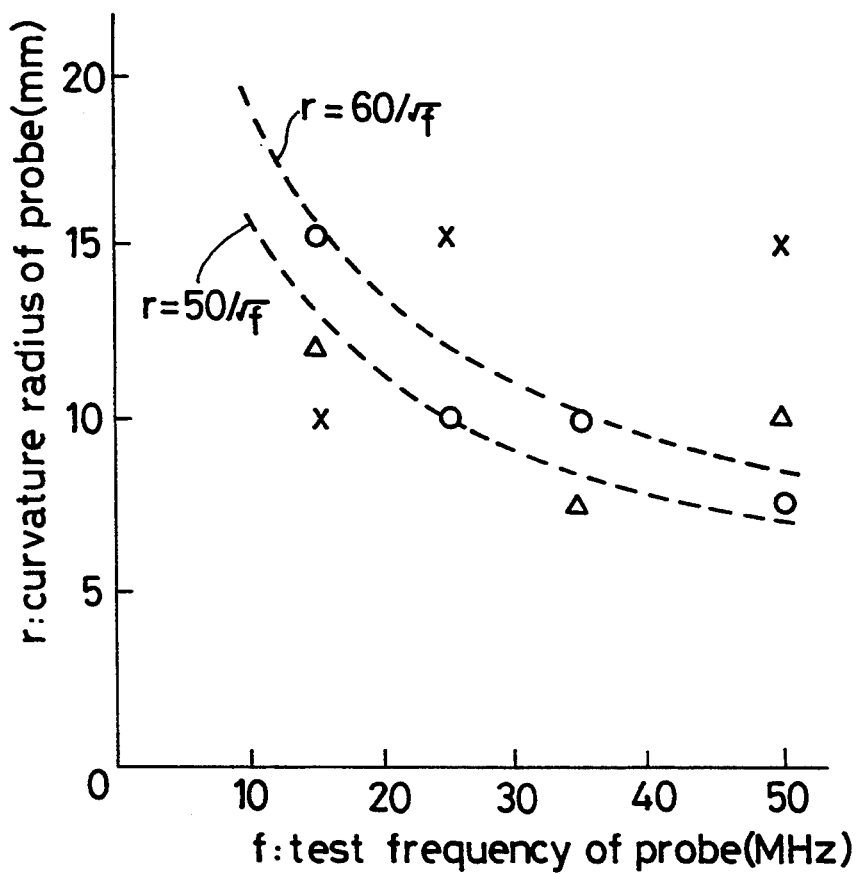
FIG. 6 is a graph showing the relationship between test frequency of the probe and radius of curvature of the probe.

Further, the relationship between the test frequency f (MHz) and the radius of curvature r (mm) of ball, based on the above experimental results, is shown in FIG. 6.

TABLE 1

| Experiment No. | Test frequency f (MHz) | Tip portion of probe | | r√f | D/r | Size of flaws detected (μm) | Evaluation |
|---|---|---|---|---|---|---|---|
| | | Radius of curvature r (mm) | Oscillator diameter D (mm) | | | | |
| 1 | 50 | 7.5 | 3 | 53 | 0.40 | All sizes | ○ |
| 2 | 50 | 10 | 5 | 71 | 0.50 | ≧100 φ | Δ |
| 3 | 50 | 15 | 6.4 | 106 | 0.43 | ≧500 φ | X |
| 4 | 15 | 15 | 6.4 | 58 | 0.43 | All sizes | ○ |
| 5 | 15 | 12 | 6.4 | 46 | 0.53 | ≧100 φ | Δ |
| 6 | 15 | 10 | 6.4 | 39 | 0.64 | ≧300 φ | X |
| 7 | 25 | 15 | 6.4 | 75 | 0.43 | ≧300 φ | X |
| 8 | 25 | 10 | 5 | 50 | 0.50 | All sizes | ○ |
| 9 | 35 | 7.5 | 3 | 44 | 0.40 | ≧100 φ | Δ |
| 10 | 35 | 10 | 5 | 59 | 0.50 | All sizes | ○ |
| 11 | 15 | 15 | 10 | 58 | 0.67 | Detection was impossible due to great noise | X |
| 12 | 25 | 10 | 3 | 50 | 0.30 | ≧300 φ | X |

Note: Of the mark used in evaluation, ○ indicates that all the flaws were detectable, Δ indicates that the flaws ranging down to 100 μm φ were detectable, and X indicates poorer results.

As is clearly seen from the results of the above embodiment, when ultrasonic testing is carried out by use of a probe which has a curved surface complementary in shape to a curved surface of the material to be tested and in which the test frequency f (MHz) and the radius of curvature r (mm) of a tip portion of the probe are set in the relationship of the above-mentioned formula (1) and the radius of curvature r (mm) of the tip portion of the probe and the oscillator diameter D (mm) are predetermined, it is possible to detect with good accuracy minute flaws in the surface and the inside of the material to be tested, particularly a ball-shaped material, which has a curved surface with a radius of curvature ranging from several tens of millimeters down to 10 mm or below.

What is claimed is:

1. A method for detecting flaws in a test material in a liquid medium using an ultrasonic probe, comprising the steps of:

positioning the ultrasonic probe so that a wave emitting surface thereof faces a curved test surface of the test material, said wave emitting surface comprising a curved wave emitting surface complementary in shape to said curved test surface of said test material;

generating ultrasonic waves toward said test material from said wave emitting surface, said ultrasonic waves having a predetermined test frequency f;

wherein said wave emitting surface of said ultrasonic probe has a radius of curvature r within a range 50 mm≦r√f≦60 mm, where f equals the value of said test frequency in MHz, and said wave emitting surface has an oscillator diameter D within a range 0.35≦D/r≦0.50 and wherein said test material comprises a ball-shaped material having a radius of curvature R, and said radius of curvature r of said wave emitting surface of the probe is from 1.0 to 3.0 times the radius of curvature R of said ball-shaped material, further comprising the step of positioning said ultrasonic probe so that a center axis of said ultrasonic probe and a center axis of curvature of said ball-shaped material are disposed eccentrically to each other, and a refraction angle of said ultrasonic waves equals substantially 90°.

2. The method according to claim 1, wherein said oscillator diameter D is within a range $0.35 \leq D/r \leq 0.43$.

3. The method according to claim 1, wherein the radius of said ball-shaped material is less than or equal to 20 mm.

4. The method according to claim 1, wherein the test material comprises a ceramic.

5. The method according to claim 1, wherein said wave emitting surface comprises an acoustic lens.

6. The method according to claim 1, wherein said wave emitting surface comprises an oscillator.

* * * * *